United States Patent [19]  [11] Patent Number: 4,582,066
Barnes et al.  [45] Date of Patent: Apr. 15, 1986

[54] ULTRASONIC TRANSDUCER PROBE

[75] Inventors: Stephen R. Barnes, Seattle; Lee L. Huntsman, Bainbridge Island; Gary L. Nichols, Issaquah, all of Wash.

[73] Assignee: Lawrence Medical Systems, Inc., Redmond, Wash.

[21] Appl. No.: 748,490

[22] Filed: Jun. 25, 1985

Related U.S. Application Data

[63] Continuation of Ser. No. 464,125, Feb. 2, 1983, abandoned.

[51] Int. Cl.⁴ .............................................. A61B 10/00
[52] U.S. Cl. ...................................... 128/661; 128/663
[58] Field of Search ................................. 128/660–663

[56] References Cited

U.S. PATENT DOCUMENTS 4,183,353  1/1980  Gallub .............................. 128/661 X
4,413,629 11/1983  Durley .............................. 128/661 X
4,433,691  2/1984  Bickman ........................... 128/660

Primary Examiner—Kyle L. Howell
Assistant Examiner—Francis J. Jaworski
Attorney, Agent, or Firm—Hughes & Cassidy

[57] ABSTRACT

An ultrasonic transducer having a transducer head, for insonifying an organ or part thereof in a human patient from a position within the suprasternal notch thereof, wherein the transducer head is in at least a partially obscured disposition within the notch vis-a-vis the operator thereof during insonification, is comprised of an elongate handle member with a proximal and a distal end, having a non-circular peripheral cross-sectional geometry including at least one longitudinal edge to yield a gripping surface providing the operator with the ability to manipulate the probe via tactile sensing of its position and a transducer head extending from the distal end of, and generally normal to, the handle, wherein the head has a generally arcuate cross-sectional geometry and a generally trapezoidal profile to enhance patient comfort during operator manipulation of the probe.

5 Claims, 10 Drawing Figures

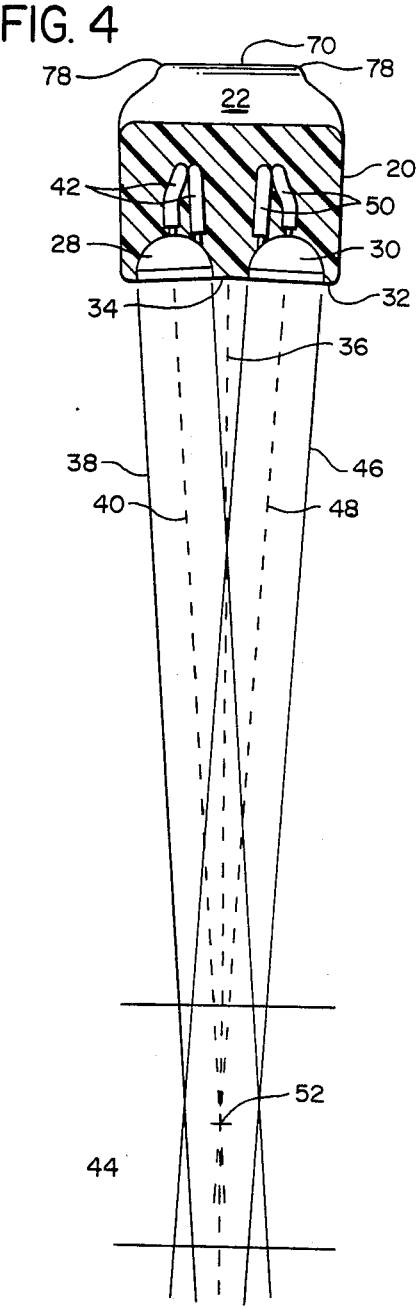
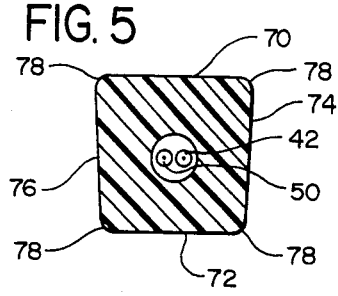
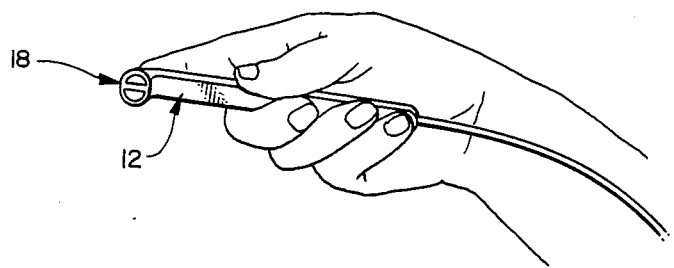
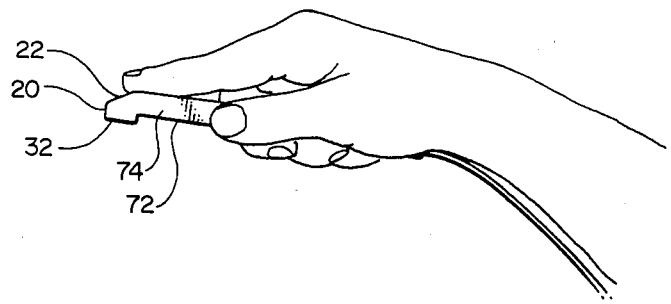

ULTRASONIC TRANSDUCER PROBE

This is a continuation of application Ser. No. 464,125, filed Feb. 2, 1983 and now abandoned.

BACKGROUND OF THE INVENTION

1. Field of the Invention

The present invention relates, generally, to ultrasonic transducer probes, more especially to continuous wave ultrasonic transducer probes, and most particularly to such a transducer probe for medical diagnostic procedures wherein the probe is positioned within the suprasternal notch of a human patient in order to insonify the ascending aorta.

2. Description of the Background Art

Insonification of mammalian organs as a medical diagnostic technique has come to the fore within the last decade. Ultrasonic energy is transmitted into a body and reflected energy from object organs, tissues, or the like within an insonified region or field is received, processed, thence analyzed as an indication of extant conditions thereof. Ultrasonic diagnostic procedures are now relatively commonplace in the examination of human patients to identify a wide range of physical conditions and/or disorders; ranging, e.g., from prenatal examinations of a fetus to the measurement of cardiac output. As will be appreciated more fully as this description ensues, it is to devices for use within the latter class that the invention is most particularly related.

Substantial attention has been paid in the art of ultrasonic diagostics to improvements in the systems employed for generating and receiving the ultrasonic energy and methods and means for analysis of the results obtained thereby. Only scant attention has been paid to the design of the transducer probe utilized in conjunction with these systems. For those systems destined for examination, e.g., of prenatal conditions where the ultrasonic transducer is applied to the abdominal region of a patient, there are very few limiting geometrical constraints on the size and shape of the transducer probe. Contrariwise, important considerations of patient comfort and operator efficiency obtain in respect of ultrasonic examination via insonification through the suprasternal notch, as is the case where cardiac output is being examined by insonification of the ascending aorta. Within that context, the patient may be in a supine position, perhaps partially elevated, while the system operator places the head of the transducer probe within the suprasternal notch and is required to manipulate that probe in order to effectuate beam steering for the purpose of positioning the transducer elements properly relative to the cardiac region. The transducer head is usually at least partially obscured from view of the operator by virtue of its disposition within the suprasternal notch. Typically, the operator is observing an output device, usually a graphic output such as a CRT, to achieve appropriate positioning of the probe; attention thus diverted from the physical placement of the probe within the notch of the patient under examination. On the other hand, the patient must remain reasonably still while the operator manipulates the probe and, accordingly, patient comfort is a requirement which should not be underestimated lest patient movement in response to discomfort may contribute to erroneous data.

To date, the art has yet to respond to the combined needs for an ultrasonic transducer probe which assists in positioning by the operator without the need for direct visual observation during manipulation while allowing for improved patient comfort during necessary manipulation while the probe is disposed within the suprasternal notch.

SUMMARY OF THE INVENTION

The present invention advantageously provides an improved ultrasonic transducer probe particularly adapted for insonification of a human patient by disposition thereof within the suprasternal notch. The improved design of the instant transducer probe presents tactile positioning means whereby the system operator may achieve appropriate positioning of the transducer head, usually at least partially obscured within the patient's suprasternal notch, while focusing attention on whatever equipment is associated with the system. Yet an additional benefit of the present design is minimization of patient discomfort otherwise heretofore associated with that type of operator manipulation, fostering a more relaxed atmosphere for the test and, in turn, enhanced reliability of the results thereof.

The foregoing, and other, advantages and benefits are realized in an ultrasonic transducer probe comprising an elongate handle member with a proximal and a distal end, having a non-circular peripheral cross-sectional geometry including at least one longitudinal edge or raised rib to yield a gripping surface providing tactile positioning means for the transducer and a transducer head extending from the distal end of, and generally normal to, the handle, wherein the head has a generally arcuate cross-sectional geometry and a generally trapezoidal profile. The non-circular cross-sectional geometry of the handle member, and most notably the edge(s) or rib(s) thereon, provide(s) the system operator with a sensory indication of the position of the transducer head even though the same is at least partially obscured within the patient's suprasternal notch, greatly facilitating beam steering during the insonification procedure. The generally arcuate cross-sectional geometry of the head, with rounded corners and the lack of edges, allows rotational manipulation of the probe within the suprasternal notch without accompanying discomfort experienced by the patient; while the generally trapezoidal profile permits lateral movement without objectionable probing discomfort. Furthermore, the juncture of the transducer head and handle member, in concert with the aforementioned geometrical configurations, yields a hook-like conformation greatly facilitating placement of the probe properly within the suprasternal notch.

In a preferred form of the present invention, the handle member has a quadrilaterial cross-sectional geometry such as a rectilinear or trapezoidal cross section; and most preferably a generally square cross section with a very slight downward and inward taper along the side edges with respect to the longitudinal axis thereof. Further along these lines, the transducer head may take any of a number of arcuate forms, the preferred being either ovate or circular as may be required by or depending on the transducer crystal array selected.

A particularly preferred transducer crystal array for a continuous wave ultrasonic probe is comprised of a transmitter cyrstal and a receiver crystal, wherein each is of a generally "D"-shape directed outwardly from the bottom face of the transducer head. In that embodiment, the two crystals are disposed in spaced relationship along the respective linear legs thereof and the same are pitched one with respect to another in order to achieve a desirable focal length. In another aspect, a single transducer crystal is employed, e.g., where the procedure utilizes a pulse echo transducer system, in which case the single crystal is preferably disposed within a transducer head having a generally circular cross section.

Other advantages, and a fuller appreciation of the construction and mode of operation of the present invention, will be gained upon an examination of the following detailed description of preferred embodiments, taken in conjunction with the figures of drawing, wherein:

DESCRIPTION OF THE DRAWINGS

FIG. 4 is a sectional view taken substantially along the line 4—4 of FIG. 2 and illustrating details of an illustrative mounting arrangement for the transmit and receive crystals in a continuous wave ultrasonic transducer and, illustrating also in broken lines, the focal point and focal zone established with the exemplary focused beam continuous wave transducer;

FIG. 5 is a sectional view taken substantially along the line 5—5 of FIG. 2, and illustrating particularly the non-circular and peferably rectilinear configuration of the transducer handle which serves to provide a sensory input for the medical practitioner assisting in aiming the ultrasonic beam;

FIGS. 6 and 7 are, respectively, bottom and side isometric views illustrating the recommended procedure for holding the ultrasonic transducer of the present invention;

DETAILED DESCRIPTION OF THE INVENTION

Figure 1:
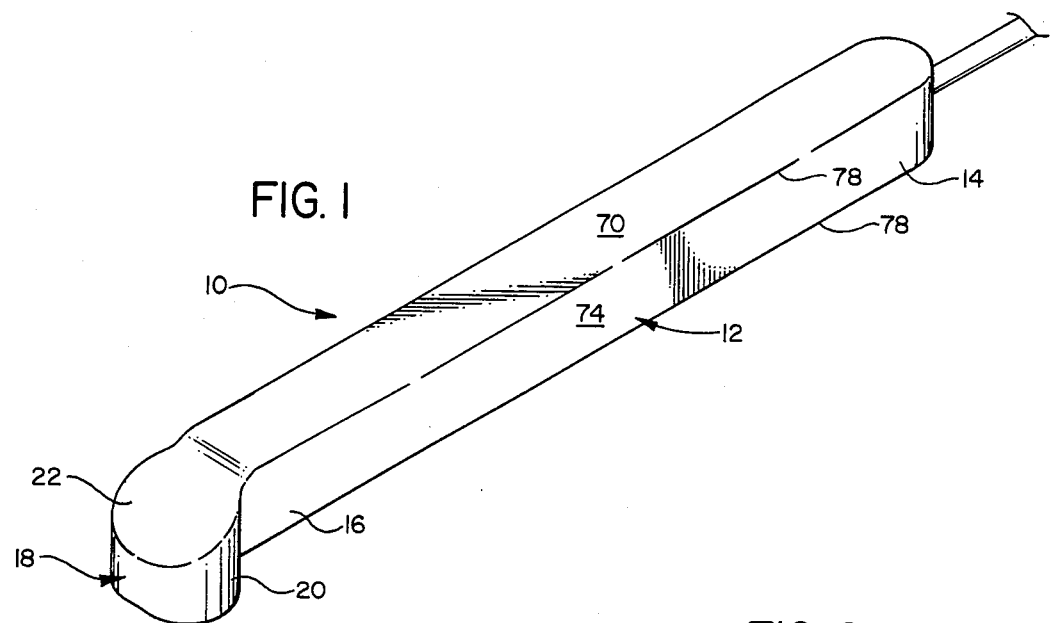
FIG. 1 is a perspective view of an ultrasonic transducer embodying the features of the present invention.

The present invention relates, generally, to ultrasonic transducer probes, more especially to continuous wave untrasonic transducer probes, and most particularly to such a transducer probe for medical diagnostic procedures wherein the probe is positioned within the suprasternal notch of a human patient in order to insonify the ascending aorta. Accordingly, the present invention will now be described with reference to certain preferred embodiments within the foregoing contexts; albeit, those skilled in the art will appreciate that such a description is meant to be exemplary only and should not be deemed limitative.

Turning to the figures of drawing, in each of which like parts are identified with like reference characters, an ultrasonic transducer probe, designated generally as 10, is shown to be comprised of an elongate handle designated generally as 12 having a proximal end 14 and a distal end 16, and a transducer head designated generally as 18 depending from the latter. As best viewed in FIGS. 1-3 (collectively) the head 18 has a generally arcuate cross section defined by an arcuate sidewall 20 tapered along the leading edge at a sloping top face 22; thereby yielding a generally trapezoidal profile as best viewed in FIG. 3. The transducer head 18 extends generally normal to the longitudinal axis of the handle 12 and projects slightly downward therefrom at a common juncture 24 in the form of a step. As will be described more fully hereinbelow, the overall geometry of the head 18 and its disposition relative to the handle 12 materially facilitates the use of the probe 10 in its most preferred environment within the suprasternal notch of a human patient.

The transducer head 18 (as is conventional) houses transducer crystal means designated generally as 26. In a highly preferred embodiment, the transducer cyrstal means 26 is composed of an array of a transmitter crystal 28 and a receiver crystal 30 generally flush with the bottom face 32 of the transducer head member. As viewed best in FIGS. 3 and 4, each of the transducer cyrstals 28 and 30 is in the general shape of a "D", where the two crystals are disposed in spaced relationship along their respective linear legs, separated by an intermediate marginal element 34 of the transducer head. Further, the bottom face 32 is formed with a slight outward bevel along the line of the marginal separator 34, as best viewed in FIG. 4. Consequently, the two transducer crystals assume a cooperative, angular relationship as respects the line of propagation of outgoing ultrasonic energy for insonification and the line of reception from the insonified region. More specifically, and with particular reference to FIG. 4, the bevel of face 32 presents the transmitter crystal 28 at an angle toward the transverse centerline 36 along a transmitter path 38 represented, for simplicity sake, by the single propagation line 40. When the transmitter crystal 28 is energized by a suitable voltage pulse via wiring leads 42, an ultrasonic wave will progress along propagation line 40 and insonify a region within the patient's body designated generally as 44. Likewise, the bevel on face 32 presents the receiver crystal at an angle with respect to the transverse centerline 36, defining a receiver path 46 represented again for simplicity sake by the single receiver line 48. Reflected sound energy from the region 44 will return along the receiver line 48 to the crystal 30, wherein the mechanical movement of the crystal is reconverted to an electrical signal conducted outwardly of the probe via receiver wiring 50. As is evident from the intersection of the propagation and receiver lines 40 and 48, respectively, along the transverse centerline 36, a focal point 52 is defined within the insonified region 44 (corresponding to the focal zone); the depth of focus being dictated, inter alia, by the pitch of face 32 and the spacing between the transducer crystals across the marginal element 34. For insonification of the ascending aorta through the suprasternal notch in order to measure cardiac output, the focal zone is preferably from about 6 to about 8 centimeters from the face 32 with a focal point midway (i.e., about 7 centimeters). A bevel angle on the order of about 3°, yielding an included angle between crystals 28 and 30 of about 174°, optimizes this focal depth.

Figure 8:
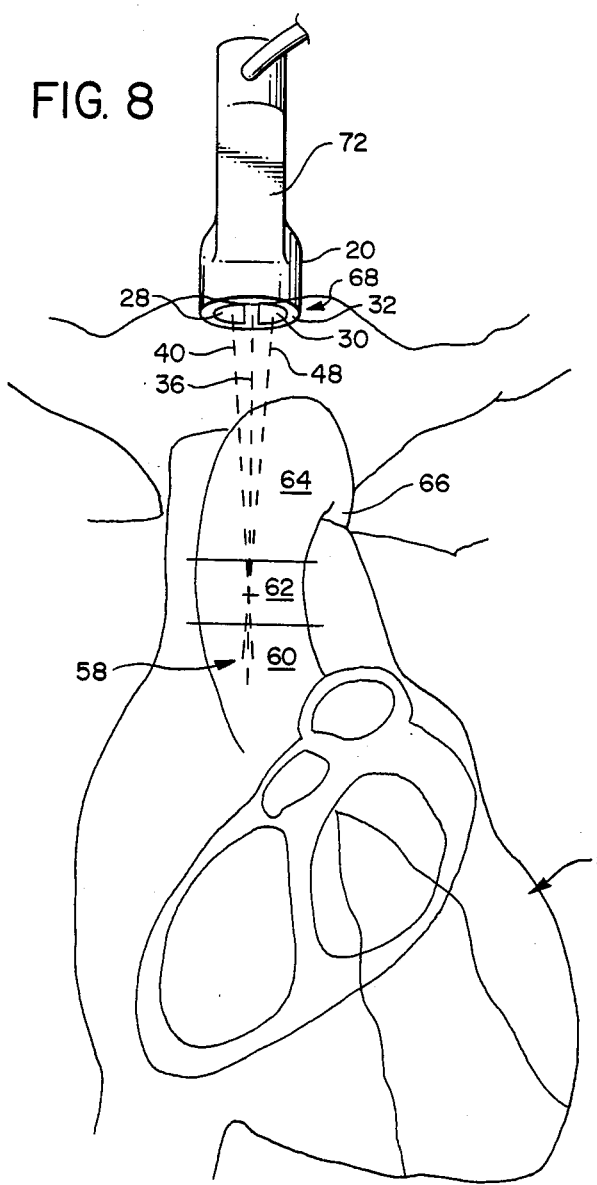
FIG. 8 is a diagrammatic frontal elevational view illustrating generally a human heart and certain of the major arterial vessels, and particularly ilustrating the relative positions of the patient's suprasternal notch and ascending aorta with the transducer of the present invention positioned in the suprasternal notch and directing a focused ultrasonic beam substantially axially along the ascending aorta.
Figure 9:
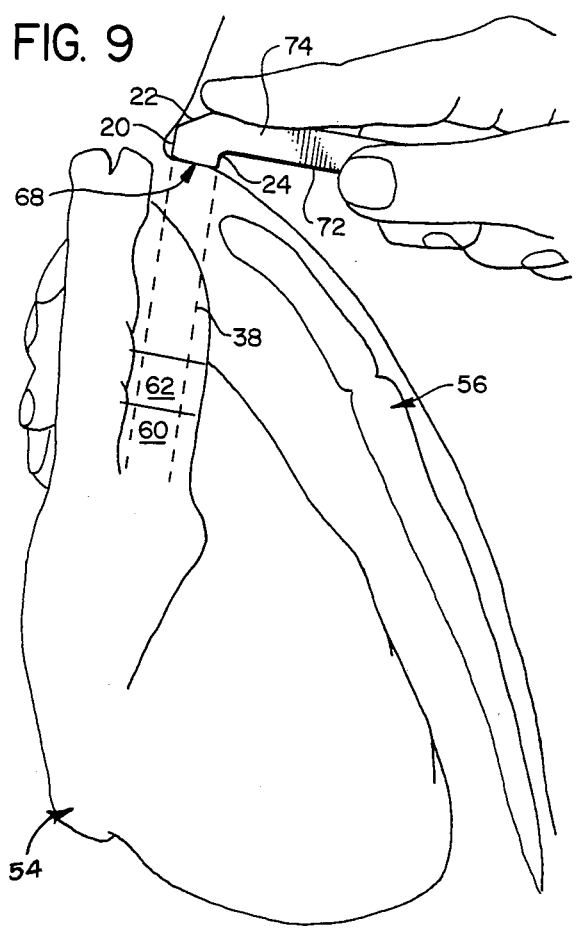
FIG. 9 is a highly diagrammatic side elevational view of the upper chest and lower neck portion of a patient in a supine position and illustrating particularly proper placement of the ultrasonic transducer of the present invention within the patient's suprasternal notch with a focused ultrasonic beam being directed substantially axially along the ascending aorta which is here illustrated diagrammatically; and, FIG. 10 is a bottom plan view similar to FIG. 3, but here illustrating a modified pulse-type ultrasonic transducer of the type employing only a single crystal which is energized to alternately function as a transmit crystal and as a receive crystal.

A principal ramification of the foregoing is the importance of positioning the transducer head 18 properly within the suprasternal notch of a patient in order to present the focal point 52 within the region of the ascending aorta as best viewed in FIGS. 8 and 9. Those figures illustrate (in a highly diagrammatic form) a heart designated generally as 54 disposed within the chest cavity posterior of a sternum designated generally as 56. For purposes of the present discussion, the important anatomical structure is the aorta, identified generally as 58, is comprised of the aortic root 60, the ascending aorta 62, the transverse aorta 64 and the descending aorta 66. A probe 10 in accordance with the present invention, like that described above with reference to, e.g., to FIG. 4, is disposed within the suprasternal notch 68 for insonification of the ascending aorta shown to be within the focal zone of the transducer. In order for the operator to locate the ascending aorta 62 properly within the focal zone of the device, the transducer probe must be manipulated within the notch 68. Usually, the operator's attention is on a visual display during this procedure limiting the ability to pay strict visual attention to the location of the probe which, as can be seen with reference to FIGS. 8 and 9, is at least partially obscured within the patient's suprasternal notch. Of equal importance during the physical manipulation of the transducer probe 10 is patient comfort. The configuration of the probe 10 accommodates these two objectives. Initial positioning of the transducer probe 10 within the suprasternal notch and subsequent, necessary manipulation is facilitated by the shape of the elongate handle member, and its cooperative interrelationship with the head 18 at the step 24, when the device is held properly by the operator. As best viewed with reference to FIGS. 1-3 and 5, the handle 12 has a non-circular peripheral cross-sectional geometry—in this exemplary embodiment, a quadrilateral shape. Thus, the handle includes a top face 70, a bottom face 72 and opposed side faces 74 and 76. By virtue of a quadrilateral configuration, longitudinal edges 78 are yielded at the juncture of adjacent faces which aid in grasping and positioning the probe properly. FIGS. 7 and 8 illustrate the proper grip of the probe 10, with the operator's hand grasping the proximal end of the probe, the forefinger resting proximate the merger of the top face 22 of the transducer head with the top face 70 of the handle, and the thumb applying gripping pressure to the sidewall 74. When so grasped, the flat surfaces of the quadrilateral cross section in combination with the longitudinal edges provide the operator with a sensory perception of the position of the transducer head through the operator's sense of touch; the configuration, therefore, defining tactile positioning means facilitating proper orientation of the transducer when disposed within the suprasternal notch 68. In turn, accordingly, the operator need not pay close visual attention to the transducer, allowing that attention to be focused on whatever display is associated with the overall system.

The most preferred quadrilateral cross section for the handle 12 is best viewed in FIG. 5 to be approximately square, but tending to trapezoidal in the sense that the side faces 74 and 76 have a very slight inward and downward taper. The slight taper has been determined to be preferable for accentuating the ability of the geometry to provide both tactile sensing means for positioning the probe and also added operator comfort. However, strictly rectilinear cross sections might be employed to equal advantage (e.g., square or rectangular), as might other polyhedral geometries. In further point of fact, some individuals may find that the simple inclusion of one or more longitudinal, raised edges or ribs formed along the handle will suffice for this functional objective. Accordingly, a generally circular cross section including one or more longitudinal ribs—to yield an overall non-circular peripheral geometry—might be utilized to this same end.

Regardless of the selection from among those cross-sectional configurations noted above to provide tactile positioning means for the probe, the head itself is configured with patient comfort in mind. Looking to FIGS. 1-3 and 8-9, it can be seen that the head 18 has a smooth, overall rounded geometry lacking distinct sharp edges. The lack of edges per se and the arcuate cross section permits rotation of the head 18 within the suprasternal notch 68 very smoothly. The trapezoidal profile, eliminating material from the extreme distal end of the probe, permits the same to nestle within the suprasternal notch and be manipulated to the proper anterior/posterior declination either without or only at the experience of minimal protrusion beyond the notch 68 into the patient's throat region.

Figure 2:
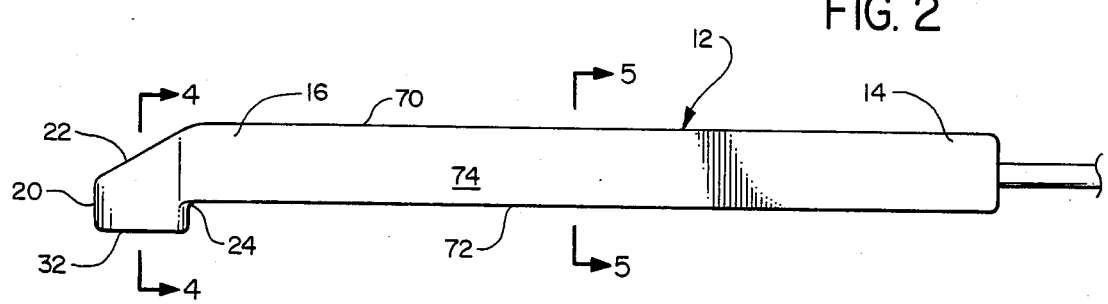
FIG. 2 is a side elevational view of the ultrasonic transducer shown in FIG. 1.
Figure 3:
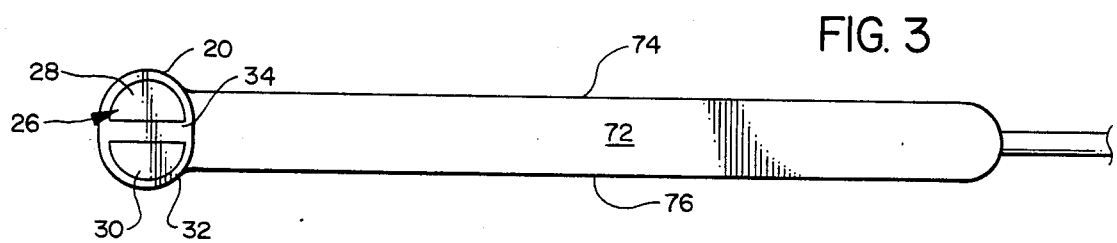
FIG. 3 is a bottom plan view of the transducer shown in FIG. 1, here illustrating the exemplary transducer as a continuous wave ultrasonic transducer of the type having a transmit crystal and a receive crystal.
Figure 10:
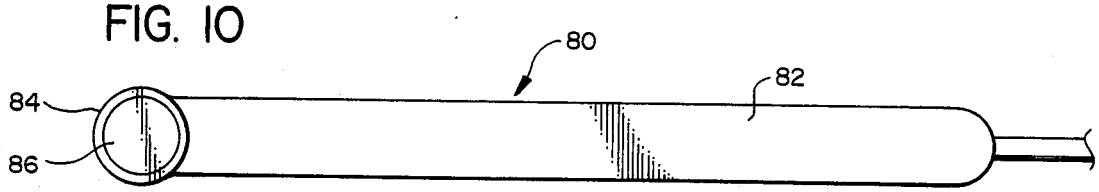

The overall arcuate cross section shown in the embodiment of FIGS. 1-9 is generally ovate, accommodating the pair of transducer crystals 28 and 30. However, it is equally well envisioned to form the transducer head in a generally circular cross-sectional configuration as viewed in FIG. 10. In that embodiment, the probe, designated generally as 80 is comprised of an elongate handle member 82, preferably of the same quadrilateral cross section as the embodiment of FIGS. 1-5. A transducer head 84 depends from the distal end of handle 82 and is formed to possess the same generally trapezoidal profile as shown in FIGS. 1 and 2. However, in this embodiment only a single transducer crystal 86 is included and, in this case, has a generally circular shape. The circular crystal is, thus, accommodated within a generally circular transducer head as opposed to the ovate head best viewed, e.g., in FIG. 3. The probe 80 is otherwise positioned and manipulated the same as the probe 10 discussed in detail above.

While the invention has now been described with reference to certain preferred embodiments, those skilled in the art will appreciate that various substitutions, modifications, changes and omissions may be made without departing from the spirit thereof. Accordingly, it is intended that the foregoing description be construed simply as illustrative of embodiments of the present invention and not be deemed limitative of the scope of the claims appended hereto.

What is claimed is:

1. An ultrasonic probe for insonifying an anatomical structure of a patient from a visually obscured position within the suprasternal notch of said patient, said ultrasonic probe comprising: an elongated handle which has a polygonal cross-sectional configuration and thereby provides a plurality of flat gripping surfaces which optimize the tactile positioning of said probe in the patient's suprasternal notch by a person handling said probe; a transducer head integral with said handle and located at one end thereof, the longitudinal axes of said transducer head and said handle being oriented at a severe angle relative to each other and said transducer head so protruding beyond the juncture between said head and said handle as to accommodate the transducer head within the suprasternal notch of the patient and permit that rectilinear and rotational manipulation of the probe needed to align a beam of ultrasonic radiation propagated from said head relative to the ascending aorta of said patient; and said transducer head having a curvilinear cross-sectional configuration and a trapezoidal profile which cooperate to so accommodate said transducer head within the suprasternal notch of the patient as to facilitate the positioning and manipulation of said probe within said suprasternal notch with a minimum of discomfort to said patient.

2. An ultrasonic probe as defined in claim 1 wherein the handle of said probe has side walls which converge toward the bottom of the handle.

3. An ultrasonic probe as defined in claim 1 wherein the transducer head of the probe has a generally circular or oval cross-sectional configuration.

4. An ultrasonic probe as defined in claim 1 wherein the end of said transducer head opposite that at the juncture with said handle has a pair of juxtaposed recesses opening onto the surface thereof and wherein said probe further comprises a pair of transducers flush-mounted in said recesses, said opposite end of said transducer head being so configured as to cant said transducers toward each other, whereby radiant energy paths extending normally from and toward different ones of said transducers converge to define a focal zone encompassing the ascending aorta of the patient so that energy propagated from one of said transducers and reflected from said aorta and blood flowing therethrough will be intercepted by the other of said transducers.

5. An ultrasonic probe as defined in claim 1 wherein those corners and edges of the probe that are adapted to come into contact with the patient or to be contacted by the person manipulating said probe are rounded to thereby avoid unpleasant tactile sensations.

* * * * *